US00PP28161P3

(12) United States Plant Patent
Valin

(10) Patent No.: US PP28,161 P3
(45) Date of Patent: Jul. 4, 2017

(54) ***BIDENS* PLANT NAMED 'TMBI 1105'**

(50) Latin Name: *Bidens ferulifolia*
Varietal Denomination: TMBI 1105

(71) Applicant: Branded Garden Products Ltd., Suffolk (GB)

(72) Inventor: Charles Valin, Ipswich (GB)

(73) Assignee: Branded Garden Products Ltd., Suffolk (GB)

( * ) Notice: Subject to any disclaimer, the term of this patent is extended or adjusted under 35 U.S.C. 154(b) by 114 days.

(21) Appl. No.: 14/756,890

(22) Filed: Oct. 26, 2015

(65) Prior Publication Data

US 2016/0143208 P1 May 19, 2016

(30) Foreign Application Priority Data

Nov. 17, 2014 (QZ) ..... PBR 2014/2964

(51) Int. Cl.
*A01H 5/02* (2006.01)

(52) U.S. Cl.
USPC ..... Plt./410

(58) Field of Classification Search
USPC ..... Plt./263.1, 410
See application file for complete search history.

*Primary Examiner* — Susan McCormick Ewoldt
*Assistant Examiner* — Karen Redden
(74) *Attorney, Agent, or Firm* — Bethany R. Roahrig; Barbara Campbell; Cochran Freund & Young, LLC

(57) ABSTRACT

A new cultivar of *Bidens* named 'TMBI 1105' is disclosed and is distinguishable by prostrate and naturally branching plant habit and numerous bicolored flowers whose centers are yellow and whose outer corolla is cream, and which are produced from spring until the onset of frost.

2 Drawing Sheets

Figure 1:
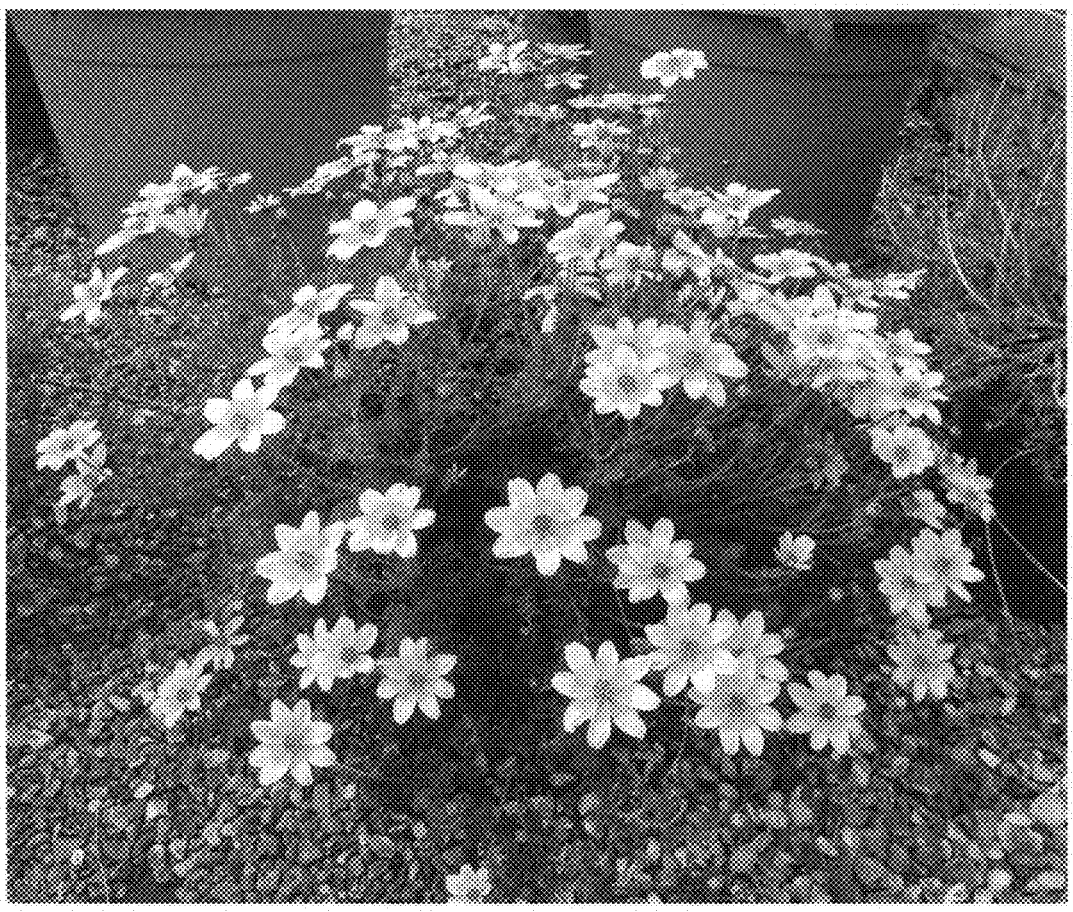

Genus and species: *Bidens ferulifolia.*
Variety denomination: 'TMBI 1105'.

CROSS REFERENCE TO RELATED APPLICATIONS

The application claims the benefit of priority under 35 U.S.C. 119(f) to European Community Plant Variety Rights application filed on Nov. 17, 2014, Application Number 2014/2964.

BACKGROUND

The present invention relates to a new and distinct cultivar of *Bidens*, a tender perennial plant which is grown for use in planted containers, hanging baskets and as an ornamental landscape plant. The new variety is known botanically as *Bidens ferulifolia* and will be referred to hereinafter by the variety name 'TMBI 1105'. *Bidens* is in the family Asteraceae whose flowers are inflorescences comprised of ray florets and disc florets. The ray florets themselves have the appearance of petals.

'TMBI 1105' is the result of a breeding program commenced in 2008 with the objective of developing unique bicolor forms of *Bidens* with either white or yellow elements. The breeding program commenced with a deliberate cross between *Bidens ferulifolia* 'Lemon Stars' (unpatented) as the female parent, and *Bidens ferulifolia* 'Pirate's Talisman' (unpatented) as the male parent. The inventor selected the most promising seedling, known to the inventor as selection code 'BI08106', for self-pollination. The inventor selected from the self-pollinated progeny of 'BI08106' one further seedling, known to the inventor as 'BI09051' which the inventor planted in the field as a potential female parent for open pollination by unnamed and unreleased selections for the male parent, each showing a bicolor characteristic and a more compact habit. The inventor collected seeds and raised seedlings from the open-pollinated female parent 'BI09051'. The raised seedlings were planted in the field in spring 2011 for continuous evaluation through spring and into summer 2011. In August 2011, the inventor selected one seedling, the present invention 'TMBI 1105', on the basis of its prostrate and naturally branching plant habit and numerous bicolored flowers whose centers are yellow and whose outer corolla is cream. The female parent of 'TMBI 1105' is the inventor's selection 'BI09051'. The male parent of 'TMBI 1105' is unknown.

'TMBI 1105' was first asexually propagated in August 2011 in an unheated greenhouse at the inventors nursery in Ipswich, Suffolk, United Kingdom. The method used for asexual propagation was direct rooting of tip cuttings. No hormone or rooting aid was employed. Subsequent asexual propagations have been carried out using tip cuttings and using stem cuttings. The inventor has determined that 'TMBI 1105' is stable and reproduces true to type in successive generations of asexual reproduction by either method of asexual propagation.

SUMMARY

The following traits have been repeatedly observed and represent the distinguishing characteristics of 'TMBI 1105'. 'TMBI 1105' has not been tested under all possible conditions and phenotypic differences may be observed with variations in environmental, climatic, and cultural conditions, without however, any variance in genotype.

1. 'TMBI 1105' exhibits a compact and naturally branching plant habit;
2. 'TMBI 1105' produces terminal inflorescences on each stem and lateral branch;

3. The ray flowers of 'TMBI 1105' are bicolored yellow and cream;
4. The yellow basal segments of each petal of 'TMBI 1105' together form a yellow eye which contrasts with the cream corolla formed by the cream tips of each petal;
5. The disc florets of 'TMBI 1105' are orange-red in color when the inflorescence is fully expanded;
6. 'TMBI 1105' blooms continually from spring until late fall;
7. After one year's growth in a one gallon container, 'TMBI 1105' is 15 cm in height and 35 cm in width;
8. As a mature plant in a frost-free landscape, 'TMBI 1105' achieves 20 cm in height and 45 cm in width; and
9. 'TMBI 1105' is hardy to USDA Zone 9.

DESCRIPTION OF THE PHOTOGRAPHS

The accompanying color photographs illustrate the overall appearance of the new *Bidens* cultivar 'TMBI 1105' showing the colors as true as it is reasonably possible to obtain in colored reproductions of this type. Colors in the photographs may differ from the color values cited in the detailed botanical description, which more accurately describes the actual colors of the new variety 'TMBI 1105'.

FIG. 1 depicts a whole plant of 'TMBI 1105' in bud and flower. The illustrated plant has been grown in a frost-free greenhouse in Ipswich, Suffolk, United Kingdom. The illustrated plant is approximately seven months old and is growing in a 25 cm diameter container without any pinching or chemical growth regulator. The photograph was taken in September 2014.

Figure 2:
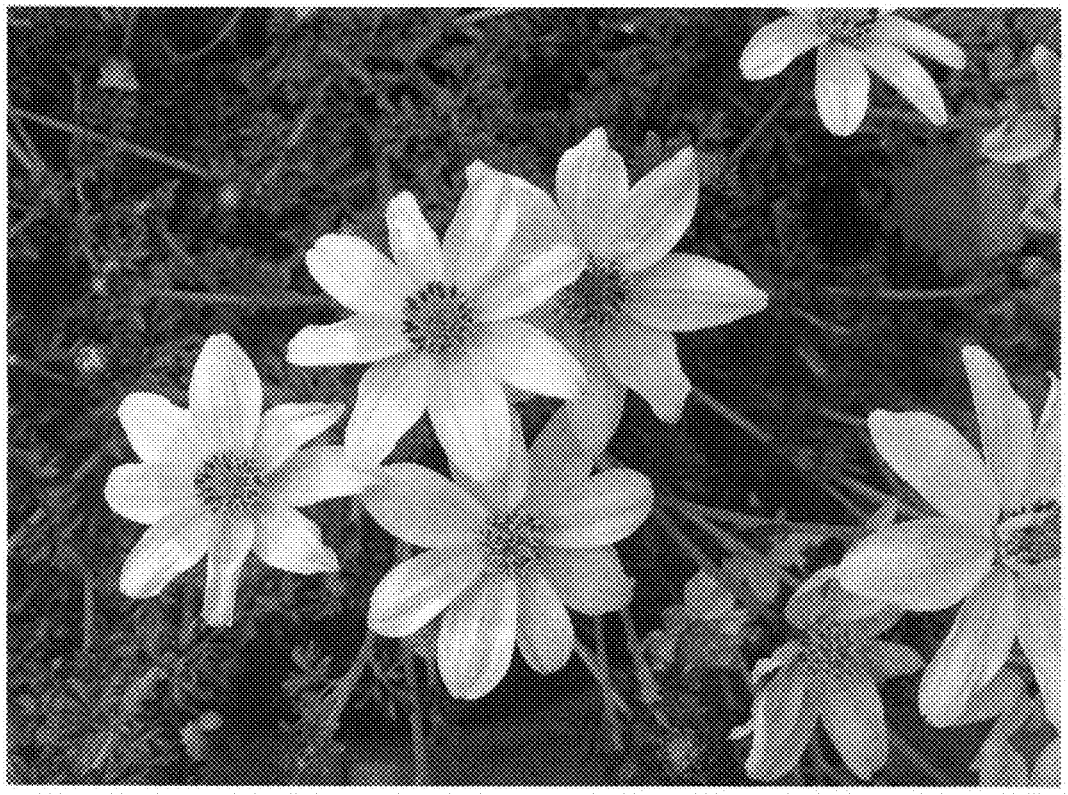

FIG. 2 depicts a close-up view of the buds and fully expanded inflorescences of 'TMBI 1105'. The photograph has been made from a close-up view of the plant illustrated in FIG. 1.

DESCRIPTION OF THE NEW VARIETY

The following detailed descriptions set forth the distinctive characteristics of 'TMBI 1105'. Observations, measurements, values, and comparisons were collected in April 2015 in Santa Barbara, Calif. from a fifteen month old plant grown outdoors in full sun in a 1 gallon container. Color determinations were made in accordance with The 2007 Royal Horticultural Society Colour Chart from London England, except where general color terms of ordinary dictionary significance are used.

Classification:

*Family.*—Asteraceae.

*Genus.*—*Bidens.*

*Species.*—*ferulifolia.*

Parentage:

*Female parent.*—*B. ferulifolia* 'BI09051' (unpatented).

*Male parent.*—Unknown *B. ferulifolia* (unpatented).

Plant:

*Propagation method.*—Tip cuttings and stem cuttings.

*Root system.*—Fine and fibrous.

*Vigor.*—Moderate vigor.

*Time to initiate roots.*—Approximately 10 to 14 days are needed to develop roots on initial cuttings.

*Temperatures to initiate rooting.*—The recommended air temperature is 20° to 21° Centigrade.

*Crop time.*—Approximately 10 weeks to 2 months are needed to produce a finished 15 cm container plant from a rooted cutting.

*Growth habit.*—Prostrate and naturally freely branching.

*Suggested container size.*—From 10 cm to 18 cm in diameter.

*Use.*—Ornamental for use in containers, hanging baskets and as a landscape plant singly or in combination with other plants.

*Type.*—Tender perennial.

*Plant dimensions.*—After one year's growth in a 1 gallon container, 15 cm in height and 35 cm in width.

*Cultural requirements.*—Grow in full sun with moderate water, and well-draining soil.

*Hardiness.*—USDA Zone 9.

*Growing requirements.*—'TMBI 1105' may be started as a cutting during December or January and will flower from spring until the onset of frost.

Stems:

*Stem shape.*—Cylindrical.

*Stem length.*—9 cm to 12 cm.

*Stem diameter.*—5 mm.

*Stem surface.*—Markedly villous with dense coverage of very fine silvery hairs, approximately 2 mm in length.

*Stem color.*—144C.

*Internode length.*—Average internode length is 15 mm to 18 mm.

Branches:

*Branching habit.*—Naturally occurring (unpinched) basal branches with lateral branches.

*Basal branches.*—Number: 6 to 8. Dimensions: 25 cm in length and 0.35 cm in diameter. Shape: Cylindrical. Surface: Densely pubescent. Hairs fine, silver-gray, length approximately 1 mm. Color: Light green 145B where not exposed to sunlight. Exposed stems exhibit red-brown streaks, color 181A. Internode length: Varies between 1.3 cm and 3.5 cm.

*Lateral branches.*—Number: 2 to 3 laterals arise from nodes along basal stems. Dimensions: 5.0 cm to 5.5 cm in length and 1.5 mm to 2.0 mm in diameter. Shape: Cylindrical. Surface: Sparsely pubescent; hairs fine, silver-gray, length less than 0.5 mm. Internode length: 1.5 cm to 1.8 cm.

Foliage:

*General description.*—Densely crispate.

*Leaf arrangement.*—Opposite.

*Type.*—Ternately compound. Each leaf consists of three trilobed leaflets.

*Leaf length.*—1.5 cm.

*Leaf width.*—1.7 cm.

*Leaf apex* (*lobe apices*).—Acute.

*Leaf base.*—Hastate.

*Leaf margins.*—Smooth, entire.

*Leaf surface* (*adaxial surface*).—Glossy, glabrous.

*Leaf surface* (*abaxial surface*).—Matte, glabrous.

*Leaf color* (*adaxial surface*).—Dark green, between 141B and 141C.

*Leaf color* (*abaxial surface*).—138A.

*Lobes.*—Shape: Deltoid. Apex: Acute. Base: Lobes are basally fused. Dimensions: 1.0 mm to 1.5 mm in length and width. Lobe margins: Smooth, entire. Lobe surface: Adaxial surface glossy, glabrous; abaxial surface matte, glabrous. Lobe color: Adaxial surface dark green, between 141B and 141C; abaxial surface 138A.

*Leaf attachment.*—Petiolate.

*Petiole shape*.—Sulcate.
*Petiole dimensions*.—6 mm in length and 1 mm in width.
*Petiole color*.—138A.
*Venation*.—None visible except leaf and leaflet appears gently folded at midrib.
*Fragrance*.—A slight sage-like scent when bruised.

Inflorescence:
*Form*.—Solitary.
*Aspect*.—Facing upward.
*Dimensions of inflorescence* (*fully expanded*).—4 mm in diameter and 1.5 cm in height.
*Type, shape*.—Radiate capitate with center disc.
*Flowering season*.—From spring until first frost.
*Fragrance*.—Absent.
*Self-cleaning or persistent*.—Self-cleaning.
*Disc diameter* (*inflorescence fully expanded*).—7 mm to 8 mm.
*Inflorescence number per plant*.—A one-year old plant bears approximately 125 inflorescences in bud and flower at one time.
*Lastingness of inflorescence on the plant*.—7 days.

Peduncle:
*Length*.—2.0 cm to 2.5 cm.
*Diameter*.—3 mm.
*Shape*.—Cylindrical.
*Texture*.—Surface is pubescent and exhibits longitudinal ridges.
*Strength*.—Very stiff and strong.
*Color*.—138C.

Flower buds:
*Surface*.—Villous.
*Height*.—1.50 cm.
*Diameter*.—3 cm.
*Shape*.—Closest to rotate whorl.
*Color*.—138B.

Ray florets:
*Shape*.—Ovate.
*Surface* (*both surfaces*).—Glabrous, adaxial surface appears glossy.
*Arrangement*.—Radiate.
*Number per inflorescence*.—7 or 8 ray florets, appearing as petals, per inflorescence.
*Fused or unfused*.—Ray florets are unfused.
*Margins*.—Entire.
*Ray floret dimensions*.—20 mm in length including the short corolla tube, 10 mm in width at the widest point, mid-way along length.
*Corolla tube dimensions*.—1.5 mm to 2 mm in length, 1 mm in diameter.
*Color*.—Each ray floret is bicolored with clear change in color halfway between apex and base and extending linearly across the leaf. When the inflorescence is fully expanded, the two colors of the ray florets are deep yellow (towards the base) and cream (towards the apex). When the inflorescence is freshly opened, the two colors are deep yellow and mid yellow.
*Ray floret color* (*expanded, adaxial surface*).—Basal half, 14A; apical half, ranges between 13D and 158D.
*Ray floret color* (*expanded, abaxial surface*).—Basal half 14C, apical half 12D.
*Ray floret color* (*freshly opened, adaxial surface*).—Basal half 14A, apical half 14C.
*Ray floret color* (*freshly opened, abaxial surface*).—Basal half 14C, apical half 13D.
*Ray floret venation*.—No veins present. Floret exhibits longitudinal raised ribs (adaxial surface) and depressions (abaxial surface).
*Phyllaries*.—Present in two concentric rings. Inner ring adnate to ray floret, 1 phyllary per floret; outer ring, 8 phyllaries held approximately 1 mm below inner phyllaries.
*Phyllary shape*.—Lanceolate.
*Phyllary dimensions*.—5 mm in length, 1 mm in width.
*Phyllary color*.—Inner phyllaries mid green 141C; outer phyllaries green-white 157D, translucent.

Disc florets:
*Quantity per inflorescence*.—Numerous, approximately 80 to 100.
*Disc floret dimensions*.—8 mm to 10 mm in length and 1.0 mm to 1.5 mm in width.
*Corolla tube*.—Appears as fused tube, unable to determine sepal component.
*Depth of disc floret corolla tube*.—4 mm.
*Color of disc florets* (*inflorescence newly opening, both surfaces*).—17C.
*Color of disc florets* (*inflorescence fully expanded, both surfaces*).—N34A.
*Sepals*.—Quantity, shape: Indeterminate. Color (as corolla tube): 157D, translucent.
*Phyllaries*.—Not observed on disc florets.

Reproductive organs (present on disc florets only):
*Stamens*.—Appear to be fused but incapable of describing individually.
*Anthers*.—Malformed, black, 1 mm in length, 0.5 mm in width.
*Pollen*.—Absent.
*Pistil*.—Style: Cylindrical, 10 mm in length including exserted stigma. Stigma: Shape, dimensions: Bifid, decurrent, each branch approximately 2 mm in length and 0.5 mm in width. Color: 23A. Ovary: Not observed.

Fruit/seed set: Not observed.

Disease and pest susceptibility: 'TMBI 1105' has not been observed to exhibit any resistance to any particular pest or disease. 'TMBI 1105' is susceptible to thrips on its flowers as may be typical of *Bidens*.

COMPARISON WITH PARENTAL LINES AND KNOWN VARIETY

'TMBI 1105' has a more compact habit than its female parent, 'BI09051'. In comparison with the female parent, the inflorescence of 'TMBI 1105' is distinctly bicolored with a yellow eye and cream corolla. The female parent has single flowers consisting of 5 petals, whereas 'TMBI 1105' has semi double flowers consisting of 7 to 8 petals.

The closest comparison plant known to the inventor is *Bidens ferulifolia* plant named 'Golden Eye', also known as KLEBF10709 (U.S. Plant Pat. No. 22,863). Whereas the flowers of 'Golden Eye' consist of 6 or 7 petals, the flowers of 'TMBI 1105' consist of 7 or 8 petals. In addition, the flowers of 'TMBI 1105' are more distinctly bicolored and the plant habit of 'TMBI 1105' is more compact than 'Golden Eye'.

I claim:

1. A new and distinct cultivar of *Bidens* plant named 'TMBI 1105' as described and shown herein.

* * * * *